US007521199B2

(12) United States Patent
Harnish et al.

(10) Patent No.: US 7,521,199 B2
(45) Date of Patent: Apr. 21, 2009

(54) ASSAY TO IDENTIFY ESTROGEN RECEPTOR DEPENDENT LIGANDS THAT REGULATE THE HEPATIC LIPASE PROMOTER

(75) Inventors: Douglas C. Harnish, Warrington, PA (US); Marshall S. Scicchitano, Douglasville, PA (US); Sotirios K. Karathanasis, Saline, MI (US); Chu-Lai Hsiao, Waltham, MA (US)

(73) Assignee: Wyeth, Madison, NJ (US)

( * ) Notice: Subject to any disclaimer, the term of this patent is extended or adjusted under 35 U.S.C. 154(b) by 170 days.

(21) Appl. No.: 11/471,781

(22) Filed: Jun. 21, 2006

(65) Prior Publication Data

US 2006/0252154 A1 Nov. 9, 2006

Related U.S. Application Data

(63) Continuation of application No. 09/924,944, filed on Aug. 8, 2001, now Pat. No. 7,094,559.

(60) Provisional application No. 60/223,647, filed on Aug. 8, 2000, provisional application No. 60/255,837, filed on Dec. 15, 2000.

(51) Int. Cl.
*C12N 15/85* (2006.01)
*C12Q 1/68* (2006.01)
(52) U.S. Cl. .................. 435/8; 435/6; 435/325; 435/368; 435/370
(58) Field of Classification Search ........................ None
See application file for complete search history.

(56) References Cited

U.S. PATENT DOCUMENTS

| 5,721,096 A | 2/1998 | Karathanasis et al. |
| 5,721,138 A | 2/1998 | Lawn |
| 5,908,859 A | 6/1999 | Cullinan et al. |
| 6,448,019 B1 | 9/2002 | Mendelsohn et al. |
| 6,465,258 B1 | 10/2002 | Shan et al. |
| 7,094,559 B1 | 8/2006 | Harnish et al. |

FOREIGN PATENT DOCUMENTS

WO WO-99/07847 2/1999

OTHER PUBLICATIONS

Ladias et al., Science, Feb. 1, 1991;251(4993):561-5.*
U.S. Appl. No. 09/924,948, Harnish et al.
U.S. Appl. No. 09/924,945, Evans et al.
U.S. Appl. No. 08/906,365, Bhat et al.
U.S. Appl. No. 10/745,379, Bhat et al.
Oet, et al., John Wiley & Sons publisher, p. 865, (1990).
Pandha, et al., Current Opinion in Investigational Drugs, 1(1):122-134 (2000).
Nuclear Receptors Nomenclature Committee, Cell, 97:161-163 (1999).
Tsai, et al., Endocrine Reviews, 18(2):229-240 (1997).
Wade, et al., Proc. Natl. Acad. Sci. USA, 90:1369-1373 (1993).
Houdebine, Journal of Biotechnology, 34:269-287 (1994).
Verma, et al., Nature, 389:239-242 (1997).
Amalfitano, et al., Current Gene Therapy, 2:111-133 (2002).
Calkhoven, et al., Eur. J. Biochem, 249:113-120 (1997).
Achatz, et al., Molecular and Cellular Biology, 17(9):4914-4932 (1997).
Boffelli, et al., J. Biol. Chem., 274: 15569-15574 (1999).
Cooney, et al., J. Virol., 65:2853-2860 (1991).
Dynan, et al., Nature, 316:774-778 (1985).
Farish, et al., Br. Med. J., 303:694 (1991).
Klinge, et al., J. Biol. Chem, 272:31465-31474 (1997).
Malik, et al., Nucleic Acids Res., 23(9):1536-1543 (1995).
Murai, et al., Atherosclerosis, 59:199 (1986).
Nunez, et al., Mol. Cell. Endocrinol., 189:191-199 (2002).
Oka, et al ., Gene, 180:69-80 (1996).
Orth-Gomer, et al., Circulation, 95:329 (1997).
Pereira, et al., J. Steroid. Biochem. Mol. Biol., 53:503-508 (1995).
Rymer, et al., Acta. Endo., 128:259 (1993).
Seed, et al., Nejm, 322:1494 (1990).
Tam, et al., Journal of Biological Chemistry, 260(3):1670-1675 (1985).
Harnish, "Estrogen Receptor Regulation of Apolipoprotein(a) Gene Promoter in HepG2 Cells", Abstract submitted for oral presentation at the Mid-Atlantic Lipid Research Symposium held on Mar. 5, 1998 (Atlantic City, NJ).
Landschulz, et al., Science, 243:1681-1688 (1989).
Birkenmeier, Genes & Development, 3:1146-1156 (1989).
Kwok, et al., Nature, 270:177-178 (abstract only) (1994).
Harnish, et al., J. Biol. Chem., 273:9270-9278 (1998).
Ameis, et al., J. Biol. Chem., 265:6552-6555 (1990).
Norris, et al., J. Biol. Chem., 270:227777-227782 (1995).
Dichek, et al., J. Biol. Chem., 273:1896-1903 (1998).
Kumar, et al., Cell, 51:941-951 (abstract only) (1987).
Kuiper, et al., Proc. Natl. Acad. Sci. USA, 93:5925 (1996).
Mosselman, et al., FEBS Letts., 392:49 (1996).
Breckenridge, et al., Atherosclerosis, 45:161 (1982).
Goldberg, et al., J. Clin. Invest. 70:1184 (1982).
Homanics, et al., J. Biol. Chem., 270:2974 (1995).
Clay, et al., Biochem. Biophys. Acta., 1002:173 (1989).
Busch, et al., J. Biol. Chem., 269:16376 (1994).
Fan, et al., PNAS, 91:8724 (1994).
Tikkanen, et al., Acta. Obstet Gynecol Scand Suppl, 88:83 (1979).

* cited by examiner (Continued)

Primary Examiner—Misook Yu
(74) Attorney, Agent, or Firm—Wilmer Cutler Pickering Hale and Dorr LLP

(57) ABSTRACT

The present invention relates to an assay system and method for testing compounds for their ability to regulate the hepatic lipase (HL) promoter. In particular, the invention relates to the identification of estrogen receptor ligands having this activity. Compounds that inhibit HL promoter activity are useful as leads, or on their own, to develop therapeutics in the prevention of heart disease.

22 Claims, No Drawings

ASSAY TO IDENTIFY ESTROGEN RECEPTOR DEPENDENT LIGANDS THAT REGULATE THE HEPATIC LIPASE PROMOTER

CROSS-REFERENCE TO RELATED APPLICATIONS

This application is a continuation of U.S. application Ser. No. 09/924,944 entitled "Assay to Identify Estrogen Receptor Dependent Ligands That Regulate the Hepatic Lipase Promoter," filed Aug. 8, 2001, now U.S. Pat. No. 7,094,559, which in turn claims priority under 35 U.S.C. §119(e) from Provisional Patent Application Nos. 60/223,647 and 60/255,837 filed on Aug. 8, 2000 and Dec. 15, 2000, respectively. Each of the above-referenced applications is incorporated by reference in their entirety.

FIELD OF THE INVENTION

The present invention relates to an assay system and method for testing compounds for their ability to regulate the hepatic lipase (HL) promoter. In particular, the invention relates to the identification of estrogen receptor ligands having this activity. Compounds that inhibit HL promoter activity are useful as leads, or on their own, to develop therapeutics in the prevention of heart disease.

BACKGROUND OF THE INVENTION

The physiological response to steroid hormones is mediated by specific interaction of steroids with nuclear receptors, which are ligand-activated transcription factors that regulate the expression of target genes. These receptors consist (in an amino-terminal-to-carboxy-terminal direction) of a hypervariable amino-terminal domain that contributes to the transactivation function; a highly conserved DNA-binding domain responsible for receptor dimerization and specific DNA binding; and a carboxy-terminal domain involved in ligand binding, nuclear localization, and ligand-dependent transactivation.

In vivo, estrogen has been identified as having utility in treating adverse behavioral/clinical symptoms that accompany fluctuations in hormones associated with menopause in aging women, although the biochemical basis for these effects has never been determined. As such, the treatment of behavioral effects with estrogen in human subjects has been restricted to the treatment of menopause in women who demonstrate signs of deficiency in estrogen, and use in prevention of the sequelae of menopause, namely hot flashes and osteoporosis, which are typically corrected by replacement therapy of estrogen.

Recently, cDNA was cloned from rat prostate and shown to have significant homology to a previously isolated rat estrogen receptor (Kuiper et al., *Proc. Natl. Acad. Sci. USA* 93:5925, 1996); this receptor was designated ERβ to distinguish it from the previously cloned receptor, ERα. Rat ERβ was shown to be expressed in prostate, testes, ovary, and thymus, in contrast to ERα, which is most highly expressed in uterus, breast, liver, and pituitary. A human ERβ homologue has been reported (*Mosselman et al.*, FEBS Letts. 392:49, 1996), having the amino-terminal sequence Gly-Tyr-Ser. A human ERβ has been described in PCT Publication WO 99/07847.

Hepatic lipase (HL) is a lipolytic enzyme that is synthesized primarily in the liver. HL hydrolyzes triglycerides and phospholipids present in chylomicron remnants, intermediate density lipoprotein (IDL), and high-density lipoprotein (HDL). Through its function as a lipolytic enzyme, HL plays a major role in the metabolism of circulating plasma lipoproteins resulting in elevation of small, dense atherogenic LDL with a decrease in HDL plasma levels. Several lines of evidence demonstrate the important role of HL in HDL metabolism. Patients with a genetic deficiency of HL have increased plasma levels of HDL cholesterol and phospholipids (Breckenridge et al, Atherosclerosis, 45:161, 1982). Increased HDL is also a hallmark of HL-deficient states induced by infusion of anti-HL antibodies (Goldberg et al., J. Clin. Invest. 70:1184, 1982), genetic manipulation (Homanics et al. J. Biol. Chem. 270:2974, 1995) or naturally present in various animal models (Clay et al. Biochim. Biophys. Acta. 1002: 173, 1989). Conversely, overexpression of HL decreases plasma HDL concentrations in transgenic mice (Busch et al. J. Biol. Chem. 269:16376, 1994) and rabbits (Fan et al. *Proc. Natl. Acad. Sci. USA* 91:8724, 1994).

In terms of ERT in postmenopausal women, it is well established that trafficking of lipoprotein cholesterol is enhanced via the reverse cholesterol transport system. HL activity has been shown to be reduced by 31% due to ERT, levels similar to that found in premenopausal women (Tikkanen et al. Acta Obstet Gynecol Scand Suppl. 88:83, 1979). Diminishment of HL activity by ERT is thought to improve the reverse cholesterol transport system by blocking the metabolism of HDL thereby maintaining higher plasma levels of HDL. In addition, inhibition of HL activity may result in a reduction in the amount of small, dense atherogenic LDL.

Thus, there is a need in the art to identify compounds that can modulate HL production. There is a further need in the art to identify compounds that can act through the estrogen receptor to modulate, and preferably inhibit, HL expression by acting on the HL promoter.

SUMMARY OF THE INVENTION

The present invention provides for a transformed cell that expresses a functional estrogen receptor, a C/EBP transcription factor, and a reporter gene that is associated with HL. In one specific embodiment, the estrogen receptor is a human estrogen receptor. In another specific embodiment, the transcription factor is C/EBPα. In another specific embodiment, the reporter gene is luciferase.

One specific embodiment provides that the cell is a hepatocarcinoma cell. In a further embodiment, the hepatocarcinoma cell is a HepG2 cell.

The present invention also provides for an assay system for estrogen ligands that modulate HL activity in a population of the transformed cells that are described above. In one specific embodiment, the estrogen receptor is a human estrogen receptor, In another specific embodiment, the transcription factor is C/EBPα. In another specific embodiment, the reporter gene is luciferase.

One specific embodiment provides that the cell is a hepatocarcinoma cell. In a further embodiment, the hepatocarcinoma cell is a HepG2 cell.

The present invention also provides for a method of identifying a compound that regulates HL promoter activity through an estrogen receptor that is expressed in the transformed cells that are described above, where a change in the level of the expression of the reporter gene indicates that the test compound regulates HL activity through the expressed estrogen receptor. The invention also contemplates a method where reporter gene expression is decreased after contact of the test compound with the assay system. In one embodiment, the test compound may be an estrogen or estrogen analog. In specific embodiments, the present invention also contemplates that the estrogen receptor is a human estrogen receptor, that the transcription factor is C/EBPα, and that HL promoter is positioned proximal to the 5' end of the HL coding region. Another specific embodiment also contemplates that the reporter gene is luciferase.

One specific embodiment provides that the cell is a hepatocarcinoma cell. In a further embodiment, the hepatocarcinoma cell is a HepG2 cell.

In one embodiment, the estrogen receptor, transcription factor, and reporter gene are expressed by separate vectors within the transformed cell.

DETAILED DESCRIPTION OF THE INVENTION

The present invention advantageously provides a transfection (or transduction) screening assay for identifying compounds that regulate hepatic lipase (HL) promoter activity through the estrogen receptor. The assay system of the invention is suitable for high throughput screening, e.g., screening thousands of compounds per assay.

The HL promoter assay can be used to identify compounds that interact with the ER to regulate HL promoter activity of a luciferase reporter construct. Compounds that inhibit HL promoter activity may result in reduced HL protein production and may be useful as novel therapeutics in the prevention of heart disease. HL is involved in lipoprotein metabolism and reduction of its activity has been associated with elevation of plasma high density lipoprotein (HDL) levels and a decrease in small, dense LDL particles which are thought to be anti-atherogenic.

The present invention is based, in part, on construction of human liver hepatoma cells, HepG2, cotransfected with (i) a human ER expression vector, (ii) a CCAAT/enhancer-binding protein (C/EBPα) expression vector, and (iii) a luciferase reporter vector in which luciferase reporter gene expression is controlled by the human HL promoter region (−1557/+43). Alternatively, (i) human ER, (ii) a C/EBPα expression vector, and (iii) a luciferase reporter vector in which luciferase reporter gene expression is controlled by the human HL promoter region are present in one vector. This vector then may be used to transform the cell.

Transfected cells in multi-well plates were treated with estrogen or test compounds for 16-24 hr and luciferase activity was determined in cell lysates. Under these conditions, 17β-estradiol inhibited HL promoter activity by approximately 75% after overnight treatment, in HepG2 cells transected with human ERα vectors. Repression of HL promoter activity is both ER and ligand dependent. Thus, the assay of the invention are applicable to other nuclear hormone receptors, including ERα receptors.

C/EBPα is a liver-enriched transcription factor which belongs to a family of receptors called CCAAT/enhancer-binding proteins, which includes C/EBPα, C/EBPβ, C/EBPγ, C/EBPδ, and C/EBPε. It induces a more differentiated phenotype in the HepG2 cells and activation of HL promoter activity by any one of these family members is also regulated by binding of an appropriate ligand to estrogen receptor.

As used herein the term "transformed cell" refers to a modified host cell that expresses (i) a functional estrogen receptor expressed from a vector encoding the estrogen receptor; (ii) a C/EBP transcription factor that acts on a HL promoter expressed from a vector encoding the transcription factor; and (iii) a reporter gene operatively associated with an HL promoter. Any host cell can be used, preferably a hepatocyte cell, and more preferably a hepatocarcinoma cell. In a specific embodiment, the cell is a HepG2 cell.

A "functional estrogen receptor" is a receptor that binds estrogen or estrogen analogs and transduces a signal upon such binding. Preferably the ER is a human ER (hER), for example hERα or hERβ. (Kioke et al. NAR 15:2499, 1987; White et al. Mol. Endo. 1:735, 1987; Kuiper et al. PNAS 93:5925, 1996; Tremblay et al. Mol Endo 11:353, 1997; Mosselman et al. FEBS Lett 392:49, 1996).

A "C/EBP transcription factor" is a liver-enriched transcription factor which belongs to a family of receptors (C/EBPα, C/EBPβ, C/EBPγ, C/EBPδ, C/EBPε). In a specific embodiment, the transcription factor is C/EBPα. CCAAT/enhancer-binding protein (C/EBP) is a transcription factor expressed primarily in liver, fat and intestinal tissues that belongs to the basic region-leucine zipper class (Birkenmeier et al. Genes & Dev. 3:1146, 1989; Landschulz et al. Science 243:1681, 1988). Overexpression of C/EBP in cotransfection assays stimulates transcription through C/EBP binding sites found in promoters of target genes and suggests that it is involved in cell type-specific expression of genes in liver, fat and possibly additional tissues.

The orphan nuclear receptor COUP-TF family members (ARP-1, EAR-2 & EAR-3) will also work however, they do not induce HL reporter activity as efficiently as CEBPα.

A "hepatic lipase" is involved in lipoprotein metabolism. The hepatic lipase promoter is the region upstream, e.g., about 1600 base pairs upstream, of the hepatic lipase coding region on the chromosome that regulates expression of the protein. HL promoter activity is regulated by ER. In a specific embodiment, the HL promoter is positioned proximal to the 5' end of the human HL coding region. In a specific embodiment, HL promoter is the human HL promoter region from −1557 to +43, relative to the HL coding region start site (0).

A "reporter gene" as used herein is a gene that encodes a detectable protein. Generally, the protein is an enzyme, and can be detected by detecting the enzymatic reaction mediated by the protein, e.g., development of a chromogenic product or light. For example, the reporter gene can encode a protein selected from the group consisting of luciferase, green fluorescent protein, yellow fluorescent protein, β-galactosidase, chloramphenicol transferase, horseradish peroxidase, and alkaline phosphatase. Alternatively, a reporter gene encodes a protein that can be detected, e.g., in an immunoassay. In a preferred embodiment, the protein encoded by the reporter gene is luminescent (fluorescent or phosphorescent). In a specific embodiment, the protein is luciferase.

The cells of the invention are particularly suitable for an assay system for estrogen receptor ligands that modulate HL promoter activity. An "assay system" is one or more collections of cells, e.g., in a microwell plate or some other culture system. To permit evaluation of the effects of a test compound on the cells, the number of cells in a single assay system is sufficient to express a detectable amount of the protein encoded by the reporter gene under conditions of maximum reporter gene expression. For example, in the absence of an estrogen that suppresses HL promoter activity, as exemplified herein by 17β-estradiol, the reporter gene expresses a detectable level of protein, such that a reduction in the level of reporter gene expression is detectable.

A "test compound" is any molecule, such as an estrogen compound, that can be tested for its ability to modulate HL promoter activity through the ER, as set forth herein.

In a specific embodiment, the term "about" or "approximately" means within 20%, preferably within 10%, and more preferably within 5% of a given value or range. Alternatively, particularly in the measurement of biological processing, the term "about" or "approximately" means within an order of magnitude, preferably within a factor of 2, of a given value, e.g., a concentration of a compound that causes a half-maximal biological effect. Thus, the term "about" or "approximately" means that a value can fall within a scientifically acceptable error range for that type of value, which will depend on how quantitative a measurement can be given the available tools.

As used herein, the term "isolated" means that the referenced material is free of components found in the natural environment in which the material is normally found. In particular, isolated biological material is free of cellular components. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes, if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate unrelated materials, i.e., contaminants. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The use of italics indicates a nucleic acid molecule (e.g., ER cDNA, gene, etc.); normal text indicates the polypeptide or protein.

Engineered ER/HL Promoter Systems

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a recombinant nucleic acid construct, such as plasmid, phage genome, virus genome, cosmid, or artificial chromosome, to which another DNA segment may be attached. In a specific embodiment, the vector may bring about the replication of the attached segment, e.g., in the case of a cloning vector. A "replicon" is any genetic element (e.g., plasmid, chromosome, virus) that functions as an autonomous unit of DNA replication in vivo, i.e., it is capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA is expressed and effects a function or phenotype on the cell in which it is expressed.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature. In the context of the present invention, the vectors for expression of the estrogen receptor, transcription factor, and reporter gene operatively associated with the HL promoter is heterologous to a host cell in which it is expressed, e.g., a hepatocarcinoma cell.

A "gene" is used herein to refer to a portion of a DNA molecule that includes a polypeptide coding sequence operatively associated with expression control sequences. In one embodiment, a gene can be a genomic or partial genomic sequence, in that it contains one or more introns. In another embodiment, the term gene refers to a cDNA molecule (i.e., the coding sequence lacking introns).

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

"Expression control sequences", e.g., transcriptional and translational control sequences, are regulatory sequences that flank a coding sequence, such as promoters, enhancers, suppressors, terminators, and the like, and that provide for the expression of a coding sequence in a host cell. In eukaryotic cells, polyadenylation signals are control sequences. On mRNA, a ribosome binding site is an expression control sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "operatively associated with" or "under the control" of transcriptional and translational control sequences in a cell when RNA polymerase transcribes the coding sequence into mRNA, which is then trans-RNA spliced (if it contains introns) and translated into the protein encoded by the coding sequence.

A "signal sequence" is included at the beginning of the coding sequence of a protein to be expressed on the surface or in the membrane of a cell. This sequence encodes a signal peptide, N-terminal to the mature polypeptide, that directs the host cell to translocate the polypeptide. The term "translocation signal sequence" is used herein to refer to this sort of signal sequence.

Recombinant vectors can be introduced into host cells via calcium phosphate precipitation, infection/viral transformation, electroporation, lipofection, etc., so that many copies of the gene sequence are generated. Preferably, the cloned gene is contained on a shuttle vector plasmid, which provides for expansion in a cloning cell, e.g., $E.$ $coli$, and facile purification for subsequent insertion into an appropriate expression cell line, if such is desired. For example, a shuttle vector, which is a vector that can replicate in more than one type of organism, can be prepared for replication in both $E.$ $coli$ and $Saccharomyces$ $cerevisiae$ by linking sequences from an $E.$ $coli$ plasmid with sequences from the yeast 2µ plasmid.

Expression Vectors

The nucleotide sequence coding for the ER and the transcription factor, i.e., a C/EBP transcription factor, can be inserted into an appropriate expression vector, i.e., a vector which contains the necessary elements for the transcription and translation of the inserted protein-coding sequence. Thus, the nucleic acid encoding ER and C/EBP are each operatively associated with a promoter in an expression vector of the invention. In addition, the reporter gene is operatively associated with the HL promoter. Both cDNA and genomic sequences can be cloned and expressed under control of such regulatory sequences. An expression vector also preferably includes a replication origin.

A wide variety of host/expression vector combinations (i.e., expression systems) may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., $E.$ $coli$ plasmids col E1, pCR1, pBR322, pMal-C2, pET, pGEX (Smith et al., Gene 67:31-40, 1988), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2µ plasmid or derivatives thereof; vectors useful in eukaryotic cells, such as vectors useful in insect or mammalian cells; vectors derived from combinations of plasmids and phage DNAS, such as plasmids that have been modified to employ phage DNA or other expression control sequences; and the like. In addition, various tumor cells lines can be used in expression systems of the invention.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells are used for screening or other assays, as described infra.

A preferred expression host is a eukaryotic cell (e.g., yeast, insect, or mammalian cell). More preferred is a mammalian cell, e.g., human, rat, monkey, dog, or hamster cell. In specific embodiments, infra, the components of the assay system (ER, C/EBP, and reporter gene under control of the HL promoter) are expressed in a hepatocarcinoma cell, specifically HepG2. Other suitable cells include, without limitation, CHO, MDCK, COS, HeLa, 3T3, and other well known cells and cell lines. Alternatively, it is possible to transfect primary cells, including primary stem cells, to generate a cell for an assay of the invention.

A recombinant ER or C/EBP, or both, protein may be expressed chromosomally, after integration of the coding sequence by recombination. In this regard, any of a number of amplification systems may be used to achieve high levels of stable gene expression (See Sambrook et al., 1989, supra).

Yeast expression systems can also be used according to the invention to express any protein of interest. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Expression of the protein or polypeptide may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. No. 5,385,839 and U.S. Pat. No. 5,168,062), the SV40 early promoter region (Benoist and Chambon, 1981, Nature 290:304-310), the promoter contained in the 3' long terminal repeat of Rous sarcoma virus (Yamamoto, et al., Cell 22:787-797, 1980), the herpes thymidine kinase promoter (Wagner et al., Proc. Natl. Acad. Sci. U.S.A. 78:1441-1445, 1981), the regulatory sequences of the metallothionein gene (Brinster et al., Nature 296:39-42, 1982); prokaryotic expression vectors such as the β-lactamase promoter (Villa-Komaroff, et al., Proc. Natl. Acad. Sci. U.S.A. 75:3727-3731, 1978), or the tac promoter (DeBoer, et al., Proc. Natl. Acad. Sci. U.S.A. 80:21-25, 1983); see also "Useful proteins from recombinant bacteria" in Scientific American, 242:74-94, 1980; promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature 315:338-340, 1985; Kollias et al., Cell 46:89-94, 1986), hematopoietic stem cell differentiation factor promoters, erythropoietin receptor promoter (Maouche et al., Blood, 15:2557, 1991), etc.

Preferred vectors, particularly for cellular assays in vitro, are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional protein can be introduced in vitro using a viral vector or through direct introduction of DNA.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 2:320-330, 1991), defective herpes virus vector lacking a glycoprotein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (J. Clin. Invest. 90:626-630, 1992; see also La Salle et al., Science 259:988-990, 1993); and a defective adeno-associated virus vector (Samulski et al., J. Virol. 61:3096-3101, 1987; Samulski et al., J. Virol. 63:3822-3828, 1989; Lebkowski et al., Mol. Cell. Biol. 8:3988-3996, 1988).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Adenovirus vectors. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (e.g., example: Mav1, Beard et al., Virology 75 (1990) 81), ovine, porcine, avian, and simian (e.g., SAV) origin. Various replication defective adenovirus and minimum adenovirus vectors have been described (WO94/26914, WO95/02697, WO94/28938, WO94/28152, WO94/12649,, WO95/02697 WO96/22378).

Adeno-associated viruses. The adeno-associated viruses (AAV) are DNA viruses of relatively small size which can integrate, in a stable and site-specific manner, into the genome of the cells which they infect. The use of vectors derived from the AAVs for transferring genes in vitro and in vivo has been described (see WO 91/18088; WO 93/09239; U.S. Pat. No. 4,797,368; U.S. Pat. No. 5,139,941, EP 488 528).

Retrovirus vectors. In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, EP178220; Bernstein et al. Genet. Eng. 7 (1985) 235; McCormick, BioTechnology 3 (1985) 689; International Patent Publication No. WO 95/07358, published Mar. 16, 1995, by Dougherty et al.; and Kuo et al., 1993, Blood 82:845. The retroviruses are integrating viruses which infect dividing cells. These vectors can be constructed from different types of retrovirus, such as, HIV, MoMuLV ("murine Moloney leukaemia virus") MSV ("murine Moloney sarcoma virus"), HaSV ("Harvey sarcoma virus"); SNV ("spleen necrosis virus"); RSV ("Rous sarcoma virus") and Friend virus. Suitable packaging cell lines have been described in the prior art, in particular the cell line PA317 (U.S. Pat. No. 4,861,719); the PsiCRIP cell line (WO 90/02806) and the GP+envAm-12 cell line (WO 89/07150).

Lentivirus vectors. In another embodiment, lentiviral vectors can be used as agents for the direct delivery and sustained expression of a transgene (for a review, see, Naldini, Curr. Opin. Biotechnol., 9:457-63, 1998; see also Zufferey, et al., J. Virol., 72:9873-80, 1998). Lentiviral packaging cell lines are available and known generally in the art (see Kim et al., J. Virology, 1998, 72:811-816). High-titer lentivirus vectors have been found to be excellent transfection agents for protein function assays in tissue cultured cells. An example is a tetracycline-inducible VSV-G pseudotyped lentivirus packaging cell line which can generate virus particles at titers greater than $10^6$ IU/ml for at least 3 to 4 days (Kafri, et al., J. Virol., 73: 576-584, 1999). The vector produced by the inducible cell line can be concentrated as needed for efficiently transducing non-dividing cells in vitro.

Non-viral vectors. In another embodiment, the vector can be introduced by lipofection, as naked DNA, or with other transfection facilitating agents (peptides, polymers, etc.). Synthetic cationic lipids can be used to prepare liposomes for transfection of a gene (Felgner, et. al., Proc. Natl. Acad. Sci. U.S.A. 84:7413-7417, 1987; Felgner and Ringold, Science 337:387-388, 1989; see Mackey, et al., Proc. Natl. Acad. Sci. U.S.A. 85:8027-8031, 1988; Ulmer et al., Science 259:1745-1748, 1993). Useful lipid compounds and compositions for transfer of nucleic acids are described in International Patent Publications WO95/18863 and WO96/17823, and in U.S. Pat. No. 5,459,127. Lipids may be chemically coupled to other molecules for the purpose of targeting (see Mackey, et. al., supra).

Other molecules are also useful for facilitating transfection of a nucleic acid, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector as a naked DNA plasmid. Naked DNA vectors can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., J. Biol. Chem. 267:963-967, 1992; Wu and Wu, J. Biol. Chem. 263:14621-14624, 1988; Hartmut et al., Canadian Patent Application No. 2,012,311, filed Mar. 15, 1990; Williams et al., Proc. Natl. Acad. Sci. USA 88:2726-2730, 1991). Receptor-mediated DNA delivery approaches can also be used (Curiel et al., Hum. Gene Ther. 3:147-154, 1992; Wu and Wu, J. Biol. Chem. 262:4429-4432, 1987).

Screening and Chemistry

The recombinant cells of the invention that express a reporter gene under control of the HL promoter, which in turn is regulated by an ER, provides for development of screening assays, particularly for high throughput screening of molecules that up- or down-regulate the activity of the reporter gene expressed under the control of HL promoter expressed after transfection or transformation of the cells. Accordingly, the present invention contemplates methods for identifying specific ligands of ER that modulate its ability to regulate the HL promoter using various screening assays known in the art.

Any screening technique known in the art can be used to screen for agonists or antagonists. The present invention contemplates screens for small molecule ligands or ligand analogs and mimics, as well as screens for natural ligands that bind to and agonize or antagonize the receptor in vivo. For example, natural products libraries can be screened using assays of the invention for molecules that agonize or antagonize HL activity via the estrogen receptor. The present invention contemplates screens for synthetic small molecule agents, chemical compounds, chemical complexes, and salts thereof as well as screens for natural products, such as plant extracts or materials obtained from fermentation broths. Other molecules that can be identified using the screens of the invention include proteins and peptide fragments, peptides, nucleic acids and oligonucleotides, carbohydrates, phospholipids and other lipid derivatives, steroids and steroid derivatives, prostaglandins and related arachadonic acid derivatives, etc. In a specific embodiment, the test compound can be an estrogen compound.

Knowledge of the primary sequence of the receptor, and the similarity of that sequence with proteins of known function, can provide an initial clue as inhibitors or antagonists. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, Science 249:386-390, 1990; Cwirla, et al., Proc. Natl. Acad. Sci., 87:6378-6382, 1990; Devlin et al., Science, 49:404-406, 1990), very large libraries can be constructed ($10^6$-$10^8$ chemical entities). A second approach uses primarily chemical methods, of which the Geysen method (Geysen et al., Molecular Immunology 23:709-715, 1986; Geysen et al. J. Immunologic Method 102:259-274, 1987; and the method of Fodor et al. (Science 251:767-773, 1991) are examples. Furka et al. (14th International Congress of Biochemistry, Volume #5, Abstract FR:013, 1988; Furka, Int. J. Peptide Protein Res. 37:487-493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., Proc. Natl. Acad. Sci. USA 90:10700-4, 1993; Ohlmeyer et al., Proc. Natl. Acad. Sci. USA 90:10922-10926, 1993; Lam et al., International Patent Publication No. WO 92/00252; Kocis et al., International Patent Publication No. WO 9428028) and the like can be used to screen for NF-E4 ligands according to the present invention.

Test compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., Tib Tech, 14:60, 1996).

In Vitro Screening Methods

According to the present invention, a recombinant ER-HL promoter activity system is constructed. Candidate agents are added to in vitro cell cultures of host cells, prepared by known methods in the art, and the activity of the reporter gene is measured. Various in vitro systems can be used to analyze the effects of a new compound on reporter gene expression under control of the HL promoter. Preferably, each experiment is performed in triplicate at multiple different dilutions of compound.

Reporter genes for use in the invention encode detectable proteins, include, but are by no means limited to, chloramphenicol transferase (CAT), β-galactosidase (β-gal), luciferase, green fluorescent protein (GFP) and derivatives thereof, yellow fluorescent protein and derivatives thereof, alkaline phosphatase, other enzymes that can be adapted to produce a detectable product, and other gene products that can be detected, e.g., immunologically (by immunoassay).

GFP has been modified to produce proteins that remain functional but have different fluorescent properties. Heim et al (U.S. Pat. No. 5,625,048) modified GFP resulting in amino-acid changes which exhibited different excitation and emission spectra with visibly distinct colors and increased intensities of emission. Bjorn et al (WO 96/23898) developed a new construct which encoded a modified GFP but also contained an enzyme recognition site. Bjorn et al (WO 97/11094) also developed new fluorescent proteins with increased intensity compared to the parent proteins. Hauswirth et al (WO 97/266333) developed a GFP protein optimized to provide higher levels of expression in mammalian cells. Gaitanaris et al (WO 97/42320) modified GFP resulting to increase the intensity of fluorescence, e.g., by some twenty times greater than wild-type GFP, therefore increasing the sensitivity of detection. Cubitt et al (WO 98/06737) developed modified GFP which could be easily distinguished from the already known green and blue fluorescent proteins. Evans et al (WO 98/21355) developed new GFP mutants excitable with blue and white light.

The host cell screening system of the invention permits two kinds of assays: direct activation assays (agonist screen) and inhibition assays (antagonist screen). An agonist screen involves detecting changes in the level of expression of the reporter gene by the host cell contacted with a test compound; generally, reporter gene expression decreases. If the reporter gene is expressed, the test compound has not affected the HL promoter via the ER; if the reporter gene expression decreases, the test compound is a candidate for developing an HL suppressive drug.

An antagonist screen involves detecting changes in the level of expression of the reporter gene by the host cell contacted with a test compound; generally, reporter gene expression is not affected or increases. If in the presence of a known ER agonist the test compound does not prevent inhibition of HL activity or increases the observed agonist HL inhibition, the test compound may not recognize the ER isoform or may be producing effects on HL activity through mechanisms other than interaction with the ER.

The reporter gene assay system described here may be used in a high-throughput primary screen for agonists and antagonists, or it may be used as a secondary functional screen for candidate compounds identified by a different primary screen, e.g., a binding assay screen that identifies compounds that interact with the receptor and affect HL promoter activity.

High-Throughput Screen

Agents according to the invention may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time (see, e.g., U.S. Pat. Nos. 5,585,277; 5,679,582; and 6,020,141). Such high-throughput screening methods are particularly preferred. Alternatively, simple reporter-gene based cell assays such as the one described here are also highly desirable. The use of high-throughput screening assays to test for agents is greatly facilitated by the availability of large amounts of purified polypeptides, as provided by the invention.

Estrogen Compounds

An "estrogen compound" is defined as any of the structures described in the 11th edition of "Steroids" from Steraloids Inc., Wilton N. H., here incorporated by reference. Included in this definition are non-steroidal estrogens described in the aforementioned reference. Other estrogen compounds included in this definition are estrogen derivatives, estrogen metabolites, estrogen precursors, and selective estrogen receptor modulators (SERMs). The term also encompasses molecules that specifically trigger the estrogen effect described herein of regulating HL promoter activity. Also included are mixtures of more than one estrogen or estrogen compound. Examples of such mixtures are provided in Table II of U.S. Pat. No. 5,554,601 (see column 6). Examples of estrogens having utility either alone or in combination with other agents are provided, e.g., in U.S. Pat. No. 5,554,601. In another embodiment, the estrogen compound is a composition of conjugated equine estrogens (PREMARIN™; Wyeth-Ayerst).

β-estrogen is the β-isomer of estrogen compounds. α-estrogen is the α-isomer of estrogen components. The term "estradiol" is either α- or β-estradiol unless specifically identified.

The term "E2," is synonymous with β-estradiol, 17β-estradiol, and β-E2. αE2 and α-estradiol is the α isomer of βE2 estradiol.

Preferably, a non-feminizing estrogen compound is used. Such a compound has the advantage of not causing uterine hypertrophy and other undesirable side effects, and thus, can be used at a higher effective dosage. Examples of non-feminizing estrogen include Raloxifene (Evista; Eli Lilly), Tamoxifen (Nolvadex; Astra Zeneca), and other selective estrogen receptor modulators.

In addition, certain compounds, such as the androgen testosterone, can be converted to estradiol in vivo.

EXAMPLE

The present invention will be better understood by reference to the following Examples, which are provided as exemplary of the invention, and not by way of limitation.

Example 1

Transformed HepG2 Cell Assay System for Compounds That Inhibit Hepatic Lipase Promoter by Binding the Estrogen Receptor Materials and Methods Human hepatocarcinoma cells (HepG2, ATCC® Cat. No. HB-8065), were grown in a 75 $cm^2$ flask in Dulbecco's modified Eagle medium (DMEM) (Gibco BRL; Rockville, Md.), supplemented with 1%, by volume, GlutaMAX™; 1%, by volume, penicillin/streptomycin; 1%, by volume, non-essential amino acids; and 10%, by volume, heat inactivated fetal bovine serum. Cell media was replaced every 2-3 days. Confluent cells were rinsed once with phosphate-buffered saline and 5 mL of a prewarmed solution comprised of about 0.05% trypsin, by volume, and about 0.5 mM ethylenediamine tetraacetic acid was added. Cells were left at room temperature for 5 minutes and cells were then dislodged from the flask by tapping the flask 50 times. Trypsinization was halted by the addition of about 8.5 mL of growth cell culture media. Cells were transferred to a test tube and centrifuged at about 300×g for about 5 minutes. Total cells were counted and resuspended at a concentration of about $1 \times 10^7$ cells/200 µL of growth cell culture media.

Resuspended cells were supplemented with 50 µg of hepatic lipase promoter plasmid (−1557 to +43), subcloned into the luciferase pGL2 reporter vector (Promega); 25 µg human estrogen receptor, which was subcloned into a pCDNA3 vector (Invitrogen); 25 µg CCAAT/enhancer-binding protein (C/EBPα) expression vector, and 20 µg β-galactosidase reporter plasmid (pCH110, Pharmacia). The mixture was transferred to a 0.2 mL BTX disposable cuvette (P/N 620). Cells were electroporated using a BTX ECM 600 (San Diego, Calif.), at 100 V, 1700 VF and 72 Ω. Cells were left a room temperature for about 20 minutes. Approximately 20.5 mL of growth cell culture media was added to the cells. Cells were then seeded at about 200 µL per well of a 96 well plate. Cells were then incubated at about 37° C. for 4 hours.

Media was aspirated and replaced with 200 µL deficient media, which was comprised of Phenol Red Free-DMEM (Gibco BRL) supplemented with 1%, by volume, glutamax; 1%, by volume, penicillin/strepomycin; 1%, by volume, non-essential amino acids; and 10%, by volume, heat inactivated, and charcoal-stripped fetal bovine serum, containing varying concentrations of estrogen test compounds. Cells were incubated at about 37° C. for 20-24 hours.

After estrogen treatment, cells were washed with phosphate-buffered saline and lysed with Cell Culture Lysis Reagent (Promega; Madison, Wis.), 50 µL/well, by shaking the plate at room temperature for about 20 minutes. From each well, 35 µL of cell lysate was transferred to a 96 lumat plate. Luciferase activity was determined by addition of 100 µL luciferase substrate and emitted light was detected with a Dentate Microfluor WHT FB using the Luciferase Assay System (Promega; Madison, Wis.). β-galactosidase activity was determined by adding 10 µL of cell lysate and 100 µL β-galactosidase light emission buffer (Tropix; Bedford Mass.) to a lumat plate. β-galactosidase activity was determined with a Microlumat LB 96P (EG&G Berthold). Emitted light, for each assay, was detected for 10 seconds.

Data were collected and analyzed with the JMP statistical program. Background RLU values were subtracted from both the luciferase and β-gal values. The data were normalized by division of the corrected luciferase values by the corrected β-gal values. Dose-response curves were generated for dose (X-axis) versus % activity (Y-axis) by analysis of data by log transformation and fitted by Huber weighting to provide efficacy (% maximal value) and potency values ($EC_{50}$) for comparison to 17-β estradiol. Mean and standard deviations were determined from at least two separate experiments with an n=4 for each experiment.

Transfected cells in multi-well plates were treated with test compounds listed in Table 1 for 16-24 hours. Luciferase activity was determined in cell lysates. Under these conditions, 17β-estradiol inhibited HL promoter activity by about 75%. Repression of HL promoter activity is ER and ligand dependent. Results are summarized in Table 1.

TABLE 1

| Compound Name | Hepatic Lipase Inhibition | |
| --- | --- | --- |
| | Efficacy$^a$ (%) | IC50 (nM) |
| 17β-estradiol | 100 | 88 |
| estrone | 95 | 26 |
| 17αΔ8,9 dehydroestradiol | — | — |
| 17β-Δ8,9-dehydroestradiol | 88 | 12 |
| Δ8,9-dehydroestrone | 93 | 10 |
| equilenin | 82 | 38 |
| 17α-dyhydroequilenin | — | — |
| 17β-dyhydroequilenin | — | — |
| equlin | — | — |
| 17α-dihydroequilin | 89 | 164 |
| 17β-dihydroequilin | 149 | 469 |
| 17α-estradiol | 69 | 457 |
| estradiene | — | — |
| raloxifene | — | — |

$^a$Efficacy is based upon a value of 100% effect of 17β-estradiol inhibition of HL activity.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

Patents, patent applications, publications, procedures, and the like are cited throughout this application, the disclosures of which are incorporated herein by reference in their entireties.

What is claimed is:

1. An isolated cell comprising:
   (i) a first exogenous nucleic acid molecule which encodes an estrogen receptor;
   (ii) a second exogenous nucleic acid molecule which encodes a chicken ovalbumin upstream promoter-transcription factor (COUP-TF); and
   (iii) a reporter operatively associated with a hepatic lipase (HL) promoter.

2. The cell of claim 1, wherein the estrogen receptor is a human estrogen receptor.

3. The cell of claim 1, wherein the estrogen receptor is an ERα.

4. The cell of claim 1, wherein the COUP-TF is selected from the group consisting of ARP-1, EAR-2, and EAR-3.

5. The cell of claim 1, wherein the estrogen receptor, the COUP-TF, and the reporter operatively associated with a hepatic lipase promoter are expressed from separate vectors, or the same vector.

6. The cell of claim 1, wherein the hepatic lipase promoter is positioned proximal to the 5' end of human hepatic lipase coding region.

7. The cell of claim 1, wherein the hepatic lipase promoter comprises the human hepatic lipase promoter region from −1557 to +43, relative to the human hepatic lipase coding region start site.

8. The cell of claim 1, wherein the reporter encodes a protein selected from the group consisting of luciferase, green fluorescent protein, yellow fluorescent protein, β-galactosidase, chloramphenicol transferase, horseradish peroxidase, and alkaline phosphatase.

9. The cell of claim 1, wherein the cell is selected from the group consisting of a yeast cell, an insect cell, and a mammalian cell.

10. The cell of claim 9, wherein the cell is a mammalian cell, and the mammalian cell is selected from the group consisting of a human cell, a rat cell, a monkey cell, a dog cell, and a hamster cell.

11. The cell of claim 1, wherein the cell is a hepatocarcinoma cell.

12. The cell of claim 1, wherein the cell is selected from the group consisting of a HepG2 cell, a COS cell, a CHO cell, a MDCK cell, a Hela cell, a 3T3 cell, and a primary cell.

13. The cell of claim 1, wherein the first and second exogenous nucleic acid molecules are inserted into expression vectors.

14. The cell of claim 12, wherein the expression vector is selected from the group consisting of pCR1, pBR322, pMal-C2, pET, pGEX, pMB9, RP4, pYES2, pYESHisA, pYESHisB, pYES HisC, pcDNA3, and a viral vector.

15. An assay system for compounds that modulate hepatic lipase promoter activity comprising a population of cells of claim 1, wherein the number of cells in a single assay system is sufficient to express a detectable amount of the protein encoded by the reporter under conditions of maximum reporter expression.

16. A method for identifying a compound that regulates an HL promoter, which method comprises detecting a change in the level of expression of a reporter in an assay system of claim 15 contacted with a test compound, wherein detection of a change in the level of expression of the reporter indicates that the test compound regulates the HL promoter.

17. The method according to claim 16, wherein the test compound is an estrogen or an estrogen analog.

18. The method according to claim 16, wherein the level of reporter expression decreases when contacted with a test compound that regulates the HL promoter.

19. The cell of claim 1, wherein the first or second exogenous nucleic acid molecules is inserted into a viral vector.

20. The cell of claim 19, wherein the viral vector is selected from the group consisting of a lentivirus vector, a retrovirus vector, a herpes virus vector, an adenovirus vector, an adeno-associated virus vector, a vaccinia virus vector, and a baculovirus vector.

21. The cell of claim 1, wherein the first and second exogenous nucleic acid molecules are inserted into a viral vector.

22. The cell of claim 21, wherein the viral vector is selected from the group consisting of a lentivirus vector, a retrovirus vector, a herpes virus vector, an adenovirus vector, an adeno-associated virus vector, a vaccinia virus vector, and a baculovirus vector.

* * * * *